United States Patent [19]

Votápek et al.

[11] 4,067,821

[45] Jan. 10, 1978

[54] METHOD OF TREATING A BIOMASS

[75] Inventors: Václav Votápek; Eduard Marval, both of Usti nad Labem; Rudolf Jílek, Brno; Karel Štamberg, Prague, all of Czechoslovakia

[73] Assignee: Ceskoslovenska komise pro atomovou energii, Prague, Czechoslovakia

[21] Appl. No.: 668,902

[22] Filed: Mar. 22, 1976

[30] Foreign Application Priority Data

Mar. 20, 1975 Czechoslovakia .................. 1867/75

[51] Int. Cl.² ............................................. C02B 1/32
[52] U.S. Cl. ...................................... 252/427; 195/54; 210/38 B
[58] Field of Search ......................... 252/427; 195/54; 210/38 B

[56] References Cited

U.S. PATENT DOCUMENTS

| 3,725,291 | 4/1973 | Serbus et al. ................ 210/38 B X |
| 3,767,790 | 10/1973 | Guttag ........................... 195/54 X |
| 3,859,210 | 1/1975 | Hatch ............................ 210/38 B X |

FOREIGN PATENT DOCUMENTS

| 2,345,430 | 4/1975 | Germany ........................ 252/427 |
| 10,628 of | 1903 | United Kingdom ................ 252/426 |

Primary Examiner—Patrick P. Garvin

[57] ABSTRACT

A technique is described for stiffening a biomass comprising mycelia fungi used for retention of heavy metal ions. The procedure involves dispersing a dry or native mycelium strain in a non-polar dispersion medium, agglomerating the resultant dispersion by adding a stiffening component and a surface active agent, and catalyzing the agglomerated mixture to yield stiffened granules.

8 Claims, No Drawings

METHOD OF TREATING A BIOMASS

This invention relates to a method for treating mycelia of fungi. More particularly, the present invention relates to a method for treating mycelia destined for use in the retention of metals.

Heretofore, procedures have been described for the use of mycelia of diverse types in the fermentation and pharmaceutical industries for the removal of metals such as uranium, radium and lead from solutions thereof. Unfortunately, early workers in the art discovered that such materials while exhibiting excellent selectivity characteristics were unsatisfactory from the standpoint of mechanical rigidity, so limiting retention and sorption mechanisms.

This prior art limitation was found to be successfully overcome by a procedure described in copending application, Ser. No. 542,515, filed Jan. 20, 1975, now U.S. Pat. No. 4,021,368. The procedure therein described involves stiffening the supporting skeleton of the mycelia, which are comprised of polysaccharide polymers, by a cross-linking mechanism utilizing a wide variety of polymerizable materials for this purpose. The mechanism of the stiffening process so described involves a block polymerization of the addition or condensation type followed by an adjustment of the granulometry of the resultant stiffened mycelia by comminution and sieving. Although this procedure has proven satisfactory, certain limitations have become apparent. Thus, it has been observed that there is an increase in formation of dust during the comminuting and sieving steps, thereby presenting a hygiene problem. Additionally, a broad spectrum of particle size results from such processing.

In accordance with the present invention these limitations are effectively obviated by a novel procedure for stiffening a biomass comprising fungi mycelia used for retention of metals, namely heavy metal ions. Briefly, the inventive technique involves dispersing a dry or native mycelium strain in a non-polar dispersion medium, under agitation. Following, the resultant dispersion is agglomerated by adding thereto stiffening components and a surface active agent in a solvent which is polar in nature and which is not miscible with the dispersion medium. Finally, a catalyst is added to the agglomerated mixture and the temperature thereof increased to at least 70° C, thereby resulting in polymerization and stiffening of the granules so formed.

It has been found that during the course of the described reaction, the agglomerates increase in mechanical strength and after a predetermined period of time can be employed as a solid sorbent for the purposes described above. From an economic standpoint, the process is particularly advantageous in that it is effected in a single unit and by suitable choice of reaction conditions such as the rotational speed of the agitator, physical characteristics of the reaction vessel and agitator as well as the rate of addition of reaction components, the granulometric composition of the final product can be controlled.

Although the prior art is replete with agglomeration and granulation techniques (see for example, O. Knacke et al, Chem. Ing.Tech, Volume 31, No. 1, page 50, 1959; J. P. Corney, Br.T.Chem.Eng. Volume 8, No. 6, Page 405, 1963 etc.) the instant technique distinguishes therefrom in the agglomeration of pulverized mycelium in a liquid continuous phase, namely, a dispersion medium.

A general discussion of the novel technique follows. It will be appreciated by those skilled in the art that the allusions to specific materials are merely for purposes of exposition and are not to be construed as limiting.

The dry pulverized mycelium selected for use herein may be of various strains. Those particularly suited for processing pursuant to the invention are Penicillium chrysogenum, Aspergillus niger, Aspergillus ochraceus 63B, Streptomyces aureofaciens, Mycellium sterilium No. 80 and the like. The dry mycellium so selected are initially added to a reaction vessel in an amount ranging up to 2 parts by weight per one part by weight of dispersion medium, containing a non-polar solvent and adapted with a suitable agitator capable of being rotated either by mechanical or electrical means at a rate within the range of 100 to 1000 r.p.m. Solvents particularly suited for this purpose are non-polar organic compounds such as xylene, chlorobenzene and the like. During this phase of the reaction complete dispersion of the mycellium in the liquid phase occurs. This is conveniently assured by the use of a dispersion medium evidencing a specific gravity similar to that of the mycellium greater than 0.7 g/sq.cm., and a boiling point which approximates the temperature required in the subsequent stiffening reaction, typically in excess of 80° C. It is also capable of forming an azeotropic mixture with water.

The next step in the process involves effective agglomeration of the dispersed mycelia. This end may be attained by adding to the latter a stiffening component, under agitation. Components suitable for this purpose are formaldehyde, formaldehyde-resorcinol, formaldehyde-urea solutions and polyvinyl acetate emulsions. Also added at this phase of the reaction is a surface active agent such as a diethanolamide of a high molecular weight fatty acid in a solvent selected from among water, ethyl alcohol and acetone. It is desirable during agglomeration to produce agglomerates having a size range of from 0.01 to 5 millimeters, such being controlled by the rate of revolution of the agitator, the volume of aqueous solution and the concentration and rate of addition thereof. The stiffening component may have a concentration ranging from 0.1 percent to saturation and the surface active agent may be used in an amount ranging from 0.0001 to 0.1 parts by weight per one part by weight of dry biomass.

Following, the reaction mixture is elevated in temperature to about 70° C during the rate stages of agglomeration and a suitable catalyst added. A useful material for this purpose is an aqueous ferric chloride solution. Finally, the polymerization reaction in the catalyzed reaction mixture is terminated and the desired granular material separated from the organic phase and dispersion medium.

A direct comparison between the process described herein and that of the copending application alluded to hereinabove reveals several striking differences. The latter involves a plurality of independent procedural steps, namely, (a) mixing of components and polymerization, (b) curing, (c) comminuting, and (d) sieving. Each of these operations is effected in an independent vessel. Accordingly, it is evident that the novel process herein is more economical and simplified, and permits the preparation of particles having a configuration and particle size more suitable for the desired application.

Illustrative examples of the present invention are set forth below. Again, it will be appreciated that the exemplary embodiments are illustrative only and are not limiting.

EXAMPLE I

A Keller flask having a capacity of 1500 ml. and being equipped with a speed controllable agitator, a continuous separator funnel and a reflex condenser was employed as a reaction vessel. 560 grams of xylene were added to the flask and while rotating the agitator at a speed of 350 r.p.m. 240 grams of finely ground mycelium of PENICILLIUM CHRYSOGENUM were added to the xylene. The resultant suspension was then heated to about 60° C at which point a solution comprising 50 grams of urea, 0.2 grams of diethanolamide of a high molecular weight fatty acid and 150 grams of a 37 per cent aqueous formaldehyde solution was added. The reaction was conducted with heating controlled so as to cease after attaining the boiling point of the reaction mixture. Next, within a 10 minute period, 2 grams of ferric chloride in 10 grams of water were added dropwise to the mixture. Vapors arising from the boiling azeotropic mixture condensed in the reflux condenser and flowed downward into the separatory funnel from which xylene was separated and recycled to the reaction flask. The aqueous phase in the condensate was discarded. Reaction continued with a temperature of 135° C was attained. Then, the mixture was cooled and reinforced mycelium in the form of granules ranging in size from 0.3 - 0.5 millimeters were separated with encapsulated filtering equipment. The yield was 285 grams of granular material having a sorptive capacity for uranium of 95.4 mg./g.

The sorptive capacity for uranium was determined in a static process as follows:

1 Gram of dry sorbent was shaken for 16 hours in a 250 ml. polyethylene medicine bottle together with 100 ml. of a $UO_2(NO_3)_2$ solution having a uranium concentration of 1 gram per liter. The sorptive capacity was calculated on the basis of uranium loss in the solution.

EXAMPLE II

The apparatus employed in example 1 was used again. 560 Grams of xylene were added to the flask and, following, 240 grams of dry finely ground mycelium of the strain PENICILLIUM CHRYSOGENUM were added, the mixture being agitated at an agitator speed of 350 r.p.m. The resultant suspension was heated to a temperature of about 60° C at which point the solution comprising 50 grams of urea, 0.1 gram of a diethanolamide of a high molecular weight fatty acid and 150 grams of 37 per cent formaldehyde were added thereto. The formaldehyde was heated so that the addition of the solution ceased after the reaction mixture attained its boiling point. Within 10 minutes, a solution of 2 grams of ferric chloride in 10 grams of water was added dropwise to the solution while the reaction mixture was heated to 135° C. Following, the mixture was cooled and the reinforced mycelium granules separated, so yielding 285 grams having a particle size ranging from 0.75 to 1.0 mm. and evidencing a sorptive capacity for uranium of 90.5 mg/g., as determined in the above-described manner.

EXAMPLE III

The procedure of Example 1 was repeated with the exception that the agitator was rotated at a speed of 600 r.p.m. The reinforced mycelium granules separated from the reaction mixture produced a yield of 285 grams having a particle size ranging from 0.1 - 0.25 mm and a sorptive capacity for uranium of 98.6 mg/g.

EXAMPLE IV

The procedure of example I was again repeated with the exception that the urea solution comprises an additional 15 grams of water. The resultant separated granular material, 285 grams, evidenced a particle size ranging from 0.75 - 1.0 mm and a sorptive capacity for uranium of 90 mg/g.

Although the invention is described with reference to a plurality of preferred embodiments thereof, it is to be expressly understood that it is in no way limited to the disclosure of such a plurality of preferred embodiments, but is capable of numerous modifications within the scope of the appended claims.

What is claimed is:

1. A method for stiffening a biomass comprising fungi mycelia which comprises the steps of:
   a. dispersing a dry mycelium strain in a non-polar organic dispersion medium by means of an agitator, the dry mycelium strain being present in an amount ranging up to 2 parts by weight of dispersion medium,
   b. effecting agglomeration of the dispersed mycelium strain by adding thereto a solution comprising a stiffening component selected from the group consisting of formaldehyde, formaldehyde-resorcinol solutions, formaldehyde-urea solutions and polyvinyl acetate emulsions, and a polar surface active agent in a solvent which is immiscible in the dispersion medium, the stiffening component having a concentration ranging from 0.1% to saturation and the surface active agent being present in an amount ranging from 0.0001 to 0.1 parts by weight per part by weight of dry biomass, and
   c. stiffening the agglomerated mixture by adding a polymerization catalyst thereto and heating the mixture to a temperature of at least 70° C.

2. A method in accordance with claim 1 wherein the non-polar dispersion medium is xylene.

3. A method in accordance with claim 1 wherein the non-polar dispersion medium is chlorobenzene.

4. A method in accordance with claim 1 wherein the surface active agent is a diethanolamide of a high molecular weight fatty acid.

5. A method in accordance with claim 1 wherein the catalyst is a ferric chloride solution.

6. A method in accordance with claim 1 wherein the rotational speed of the agitator ranges from 100 to 1000 r.p.m.

7. A method in accordance with claim 1 wherein the dispersion medium is capable of forming an azeotropic mixture with water having a boiling point in excess of 80° C and a specific gravity greater than 0.7 g/sq. cm.

8. A method in accordance with claim 1 wherein the solvent is selected from the group consisting of water, ethyl alcohol and acetone.

* * * * *